United States Patent [19]

Gindler

[11] 4,273,556

[45] Jun. 16, 1981

[54] DETERMINATION OF UREA

[75] Inventor: E. Melvin Gindler, Union City, Calif.

[73] Assignee: Sherwood Medical Industries Inc., St. Louis, Mo.

[21] Appl. No.: 105,207

[22] Filed: Dec. 19, 1979

[51] Int. Cl.$^3$ ............................................. G01N 33/62
[52] U.S. Cl. .................................. 23/230 B; 23/924; 252/408
[58] Field of Search ................. 23/230 B, 230 R, 924; 252/408

[56] References Cited

U.S. PATENT DOCUMENTS

| | | | |
|---|---|---|---|
| 3,427,225 | 2/1969 | Harvill | 23/230 B X |
| 3,890,099 | 6/1975 | Jung | 23/230 B |
| 4,074,972 | 2/1978 | Denney | 23/230 B |
| 4,105,408 | 8/1978 | Denney | 23/230 B |
| 4,119,405 | 10/1978 | Lam | 23/230 B |
| 4,131,425 | 12/1978 | Denney | 23/230 B |
| 4,131,429 | 12/1978 | Denney | 23/230 B |
| 4,131,430 | 12/1978 | Denney | 23/230 B |

OTHER PUBLICATIONS

Jung et al., "New Colorimetric Reaction for End Point, Continuous Flow and Kinetic Measurements of Urea," *Clin. Chem.*, vol. 21, No. 8 at 1136–1140 (1975).

Goodwin et al., "Spectrophotometric Quantification of Glycine in Serum and Urine," *Clin. Chem.*, vol. 19, No. 9 at 1010–1015, 1973.

*Primary Examiner*—Arnold Turk
*Attorney, Agent, or Firm*—Wegner, Stellman, McCord, Wiles & Wood

[57] ABSTRACT

Colorimetric urea determination method and reagent in which urea in a liquid sample reacts with o-phthalaldehyde and chromotropic acid or one of its salts to produce an intensely colored reaction product whose concentration is linearly related to the concentration of urea in the sample and which follows Beer's law over a wide range of urea concentrations.

19 Claims, No Drawings

DETERMINATION OF UREA

BACKGROUND OF THE INVENTION

1. Field of the Invention

This invention relates to a method of assaying urea and, more particularly, this invention relates to a colorimetric urea determination method and reagent especially suitable for assaying the urea concentration in body fluids.

2. Description of the Prior Art

Colorimetric methods of urea determination utilizing o-phthalaldehyde and a chromogenic compound are well known. Jung U.S. Pat. No. 3,890,099 (June 17, 1975) and Jung et al. "New Colorimetric Reaction for End Point, Continuous Flow, and Kinetic Measurement of Urea" (*Clin. Chem.*, Vol. 21, No. 8 at 1136–40, 1975) describe a urea determination method and reagent wherein o-phthalaldehyde and a chromogenic compound are mixed with a urea-containing liquid sample.

The o-phthalaldehyde reacts with urea to produce a substantially colorless isoindoline derivative intermediate having one or both of two alternate structures.

The chromogenic compound, N-(1-naphthyl) ethylenediamine dihydrochloride, reacts with the intermediate to form a colored reaction product of unknown structure, the concentration of which is reportedly linearly related to the urea concentration of the sample and which follows Beer's law. The concentration of the colored substance is colorimetrically determinable at an absorbance maximum position of 505 nm. N-(1-naphthyl) ethylenediamine dihydrochloride has the following structure:

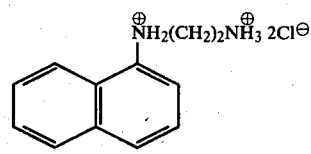

Denney U.S. Pat. No. 4,105,408 (Aug. 8, 1978), the details of which are hereby incorporated by reference, discloses five classes of chromogenic compounds which may be substituted for the chromogenic compound of the Jung disclosure. One of the classes of chromogenic compounds disclosed by Denney comprises 1, or 1,3 mono- or disubstituted hydroxy or methoxy naphthalene compounds having the following general structure:

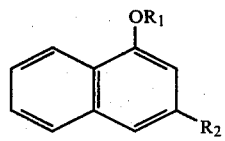

where $R_1 = -H$ or $-CH_3$ and $R_2 = -H$ or $-OCH_3$, or $-OH$. A preferred chromogenic compound of Denney is 1,3 dihydroxynaphthalene.

Each of the foregoing systems suffers from several disadvantages. According to Denney U.S. Pat. No. 4,105,408 (see col. 3, 1. 64–col. 4, 1. 21), the chromogenic compound of Jung is synthesized from α-naphthylamine, a known carcinogen, and therefore may contain at least trace amounts thereof. Furthermore, since the Jung reagents are conventionally stored in acidic solution, it is possible that the chromogen may decompose to form its carcinogenic precursor, α-naphthylamine. Also, the Jung reagents are reportedly interfered with by a variety of sulfa drugs, at least some of which are commonly present in body fluids subject to urea analysis.

Although the Denney reagents are not derived from a known carcinogen, several disadvantages are encountered with the Denney system. Firstly, it is believed that aqueous 1,3-naphthalene diols exhibit only limited stability in the presence of acid, rendering it impossible to store an acidic working reagent solution for an extended period of time. Unsubstituted 1,3-naphthalene diols are readily transported across all membranes, thereby increasing the risk of toxicity to laboratory personnel. Also, it is believed that 1,3-naphthalene diols may be interfered with to a significant extent by sulfa drugs and other drugs sometimes found in human body fluids.

SUMMARY OF THE INVENTION

According to the present invention, chromotropic acid or one of the salts, especially its disodium salt, is utilized as a chromogenic compound in an o-phthalaldehyde-based colorimetric urea determination method. The method produces an intensely colored yellow substance, the concentration of which is linearly related to urea concentration in a liquid sample, and which follows Beer's law and is therefore readily measurable by standard colorimetric techniques.

The reagent system of the invention exhibits enhanced stability relative to prior systems and requires only a single working reagent. The reagents are highly soluble in water and are less toxic than prior reagents, and exhibit little or no interference from sulfa and other drugs sometimes found in human body fluids.

DETAILED DESCRIPTION OF THE INVENTION

According to the present invention, o-phthalaldehyde reacts in an acidic medium with urea present in a liquid sample to form a substantially colorless isoindoline derivative concentrate, according to the following:

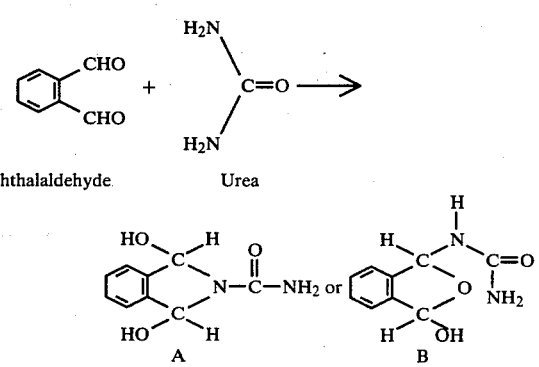

A chromogen comprising chromotropic acid or one of its salts reacts with either intermediate (form A or B) to produce an intensely colored substance of unknown structure whose concentration is linearly related to urea concentration, and which follows Beer's law over a wide range of urea concentrations.

Chromotropic acid (4,5-dihydroxynaphthalene-2,7-disulfonic acid) has the following structure:

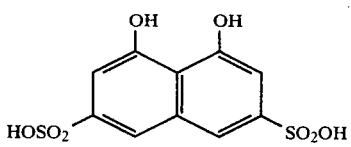

Chromotropic acid is preferably used in salt form. The disodium salt of 4,5-dihydroxynaphthalene-2,7-disulfonic acid dihydrate is especially preferred.

In the practice of the invention, a urea containing liquid sample is added to a working reagent comprising an acidic solution of o-phthalaldehyde and chromotropic acid or a salt thereof. The reagent preferably contains sulfuric acid, and may contain one or more surfactants. Only about 3 ml of working reagent is required for each 10 μl of sample.

The working reagent is preferably prepared by mixing a first aqueous reagent solution comprising o-phthalaldehyde, sulfuric acid and a surfactant, with a second aqueous reagent solution comprising chromotropic acid (or a salt thereof), a surfactant, and sulfuric acid.

Upon mixing of the urea-containing liquid sample with the working reagent, the o-phthalaldehyde and urea react to form the isoindoline derivative intermediate, as described above, which in turn reacts with the chromotropic acid to produce an intensely colored substance of unknown structure whose concentration is linearly related to the urea concentration in the sample and which follows Beer's law. The concentration of the colored substance is therefore readily determinable by spectrophotometry.

The presence of such surfactants as Armak Ethomeen ® C/25 and Bion ® NE-23, for example, is desirable in order to prevent protein precipitation and to enhance the flow properties of the reagent system.

The color-forming reaction is conveniently carried out at between about 25° C. and 37° C., preferably at 37° C., and may be conducted at temperatures as low as room temperature. The method and reagent of the invention is suitable for end point, continuous flow, and kinetic urea measurement. Due to the presence of surfactants and the properties imparted by the sulfonic acid groups of chromotropic acid, the reagent of the invention is particularly suitable for use in analytical systems having flow-through cuvettes. The reagent tends to maintain the cleanliness of the cuvettes, and will not attack polymeric cuvette materials, even after long exposure.

The reagent is suitable for use in virtually any colorimetric instrument having incubation facilities with programmed temperatures, or in equipment having constant temperature equipment, such as a constant temperature bath or block.

It has been found that, in the practice of the invention, maximum absorbance occurs at between about 440–450 nm at 37° C. The color-forming reaction is rapid; after a reaction time of less than about 20 minutes, the colored reaction product follows Beer's law over the range of at least 0–80 mg urea nitrogen/dl.

The invention is especially useful for analysis of urea in many substantially colorless body fluids, such as urine, spinal fluid, blood serum and blood plasma, or in some naturally colored body fluids such as whole blood, for example. To analyze naturally colored fluids, an absorbance reading should be taken immediately before the reaction starts, and 20 minutes after initiation of the reaction. The difference in absorbance readings corresponds to the concentration of the colored reaction product.

The reagent of the invention is highly soluble in aqueous solutions under a wide variety of conditions. It is believed that solubility is enhanced by the presence of two sulfonic acid groups on the chromotropic acid molecule. Furthermore, the reagent's relatively high stability is believed to be a result of the presence of the two highly electrophilic sulfonic acid groups, which tend to offset the nucleophilic character of the hydroxy groups present on the chromotropic acid molecule.

Several advantages are believed to derive from the use of a chromotropic acid chromogen. Aqueous acid solutions of 1,3-naphthalenediol and o-phthalaldehyde exhibit only limited stability. Therefore, prior systems utilizing naphthalenediol chromogens require that the chromogenic compound be packaged in concentrated form in a nonaqueous medium, such as alcohol, and that, when ready for use, it be added to an aqueous diluent containing sulfuric acid and a surfactant.

In prior systems, the dilute aqueous naphthalene diol solution is mixed with the o-phthalaldehyde solution immediately prior to use. Thus, prior naphthalenediol-/o-phthalaldehyde systems require that three distinct solutions be mixed, generally shortly before use.

The reagents of the invention, on the other hand, are highly stable in aqueous acidic solutions. The chromotropic acid component may be packaged in aqueous acid solution for addition to an aldehyde solution to form the working reagent. Thus, only two solutions are required.

The working reagent is highly stable, and need not be prepared immediately before use, but may be stored for a period of at least several days at room temperature.

It is believed that the working reagent of the invention is relatively nontoxic due to the presence of two sulfonic acid groups on the chromotropic acid molecule, making the molecule unlikely to cross cell membranes.

As a hindered molecule, chromotropic acid experiences relatively little, if any, interference from common drugs such as sulfa drugs and sulfonyl ureas, which are widely used antidiabetic drugs.

EXAMPLES

EXAMPLE 1—Preparation of Working Reagent

A. O-phthalaldehyde Reagent Solution

An o-phthalaldehyde solution is prepared by mixing 1.95 g o-phthalaldehyde, 81.0 ml concentrated (19 M) sulfuric acid, and 0.665 g Brij ® 35. The volume of solution is brought to 1 liter by addition of deionized water. Brij ® 35 is a polyether derived from lauryl alcohol having 23 ethylene oxide units per molecule.

B. Chromogenic Compound Solution

To a quantity of deionized water is added 49.05 g Armak Ethomeen ® C/25, 54.3 g of Pluronic ®25R 8 surfactant, 26.2 g boric acid, 16.45 g disodium salt of 4,5-dihydroxynaphthalene-2,7-disulfonic acid dihydrate, and 16.45 ml concentrated (19 M) sulfuric acid. Ethomeen ® C/25 comprises cocoamine having 15 ethylene oxide units per molecule, and effectively prevents protein precipitation in the system. The use of Pluronic ® surfactant is optional, and eliminates turbidity. The volume of solution is brought to 1 liter by addition of deionized water.

C. Working Reagent

A working reagent suitable for use in practice of this invention is prepared by mixing together equal volumes of the foregoing o-phthalaldehyde reagent and chromogenic compound solutions.

EXAMPLE 2—Analysis of Urea Nitrogen

A. Calibration Graph

The spectrophotometer used in this example was a Gilford Model 300-N having a stirred constant temperature water bath. Absorbance measurements were taken after a reaction time of about 20 minutes at 37° C.

Maximum absorbance for the reagent system was determined by obtaining readings for a standard solution containing 25 mg/dl urea nitrogen at wavelengths varying between 400 and 500 nm, spaced at 5 nm intervals. 4 ml of the working reagent of Example 1 was added to 50 μl of the 25 mg/dl standard. The absorbance maximum was obtained at approximately 445 nm, and the absorbance level between about 440 and 450 nm was substantially constant.

A series of standard urea solutions containing 0, 20, 40, 60, 80 and 100 mg/dl urea nitrogen was prepared. Absorbance readings were obtained at 37° C. and 450 nm. The absorbance readings were substantially linearly related to urea nitrogen concentration, and a linear calibration graph was plotted therefrom.

B. Determination of the Urea Nitrogen

A series of solutions, each solution containing an unknown amount of urea nitrogen, was prepared. 10 μl of each solution was mixed with 3.0 ml of the working reagent of Example 1, and the resulting solutions were incubated at 37° C. for 20 minutes and then transferred to a room temperature (22° C.) water bath.

After 5 minutes at 22° C., the absorbance of each solution at 450 nm was read in a Gilford 300-N spectrophotometer. The absorbance readings were compared with the calibration graph of Example 2(A), and urea nitrogen values were determined therefrom. The concentration values thus obtained were substantially identical to the urea nitrogen concentration in the samples as determined independently by a diacetylmonoxime method.

The foregoing detailed description is given for clearness of understanding only, and no unnecessary limitations are to be drawn therefrom, as modifications will be obvious to those skilled in the art.

I claim:

1. A method of determining the urea concentration of a liquid sample comprising the steps of:
    (a) adding o-phthalaldehyde and a chromogenic compound to said liquid sample, said chromogenic compound being chosen from the group consisting essentially of chromotropic acid and its salts;
    (b) maintaining said sample at a temperature at which said chromogenic compound, said o-phthalaldehyde and said urea in said sample react to produce a colored reaction product;
    (c) obtaining a colorimetric absorbance reading for said sample; and
    (d) comparing said absorbance reading with calibration means.

2. The method of claim 1 wherein said chromogenic compound comprises chromotropic acid.

3. The method of claim 1 wherein said chromogenic compound comprises the disodium salt of chromotropic acid.

4. The method of claim 1 wherein the formation of said colored reaction product is carried out at approximately 25° C. to 37° C.

5. The method of claim 1 wherein the formation of said colored reaction product is carried out in slightly acidic solution.

6. A method of determining the urea concentration of a liquid sample comprising the steps of
    (a) adding said liquid sample to a sample container;
    (b) adding equal amounts of o-phthalaldehyde to said sample container and to a blank container;
    (c) adding equal amounts of a chromogenic compound to the contents of each of said sample and blank containers, said chromogenic compound being chosen from the group consisting essentially of chromotropic acid and its salts;
    (d) maintaining the contents of each of said sample and blank containers in a temperature at which said chromogenic compound, said o-phthalaldehyde and said urea in said sample react to produce a colored reaction product;
    (e) obtaining colorimetric absorbance readings for the contents of each of said sample and blank containers;
    (f) computing the difference between said obtained absorbance readings; and
    (g) comparing said difference with calibration means.

7. The method of claim 6 wherein the formation of said colored reaction product is carried out at approximately 25° C. to 37° C.

8. The method of claim 6 wherein the formation of said colored reaction product is carried out in slightly acidic solution.

9. A reagent for colorimetric urea determination, said reagent consisting essentially of an acidic solution of (1) o-phthalaldehyde and (2) a chromogenic compound selected from the group consisting essentially of chromotropic acid and its salts.

10. The reagent of claim 9 wherein said chromogenic compound comprises chromotropic acid.

11. The reagent of claim 9 wherein said chromogenic compound comprises the disodium salt of chromotropic acid.

12. The reagent of claim 9 further including a surfactant.

13. A method of indicating the presence of urea in a sample, said method comprising the steps of mixing said sample with a reagent comprising o-phthalaldehyde and a chromogenic compound to produce a colored reaction product, said chromogenic compound being selected from the group consisting essentially of chromotropic acid and its salts.

14. The method of claim 13 wherein said chromogenic compound comprises chromotropic acid.

15. The method of claim 13 wherein said chromogenic compound comprises the disodium salt of chromotropic acid.

16. A reagent kit for colorimetric determination of urea, said reagent kit consisting essentially of a package containing a first container containing a first solution comprising a colorimetric amount of a chromogen chosen from the group consisting of chromotropic acid and its salts, and a second container containing a second solution comprising a colorimetric amount of o-phthalaldehyde.

17. The kit of claim 16 wherein said chromogen is chromotropic acid.

18. The kit of claim 16 wherein said chromogen is the disodium salt of chromotropic acid.

19. The kit of claim 16 wherein said first solution comprises an acidic aqueous solution of said chromogen.

* * * * *